United States Patent
Wiesner (10) Patent No.: US 10,251,818 B2
(45) Date of Patent: Apr. 9, 2019

(54) FEED-FORTIFY ENTERAL FEEDING AND RELATED METHODS THEREFOR

(71) Applicant: KPR U.S. LLC

(72) Inventor: Joel David Wiesner, St. Peters, MO (US)

(73) Assignee: KPR U.S., LLC, Mansfield, MA (US)

(*) Notice: Subject to any disclaimer, the term of this patent is extended or adjusted under 35 U.S.C. 154(b) by 386 days.

(21) Appl. No.: 14/818,374

(22) Filed: Aug. 5, 2015

(65) Prior Publication Data
US 2016/0045399 A1    Feb. 18, 2016

Related U.S. Application Data (60) Provisional application No. 62/036,194, filed on Aug. 12, 2014.

(51) Int. Cl.
*A61J 15/00*    (2006.01)

(52) U.S. Cl.
CPC ....... *A61J 15/0076* (2015.05); *A61J 15/0088* (2015.05); *A61J 15/0092* (2013.01); *A61J 2200/76* (2013.01); *A61M 2240/00* (2013.01)

(58) Field of Classification Search
CPC ............ A61J 15/0076; A61J 15/0088; A61J 15/0092; A61J 2200/76; A61M 2240/00
See application file for complete search history.

(56) References Cited

U.S. PATENT DOCUMENTS

| | | | | |
|---|---|---|---|---|
| 2009/0191066 A1* | 7/2009 | Knauper | ........... | A61M 5/14232 417/44.1 |
| 2010/0030133 A1* | 2/2010 | Elia | ........... | A61B 5/037 604/28 |
| 2014/0031784 A1* | 1/2014 | Flynn | ........... | G06F 19/3468 604/500 |
| 2014/0242213 A1* | 8/2014 | McCarty | ........... | A61J 9/00 426/2 |
| 2015/0088304 A1* | 3/2015 | Ameye | ........... | A47J 31/404 700/233 |

FOREIGN PATENT DOCUMENTS

WO    2015031714 A1    3/2015

OTHER PUBLICATIONS

International Search Report dated Nov. 5, 2015 in related International Application No. PCT/US2015/044121, 7 pages.
Written Opinion of the International Searching Authority dated Nov. 5, 2015 in related International Application No. PCT/US2015/044121, 6 pages.

* cited by examiner

*Primary Examiner* — Lauren P Farrar
(74) *Attorney, Agent, or Firm* — Adnan H. Bohri (57) ABSTRACT

A pump set for use with a pumping apparatus to deliver nutrition to an infant is disclosed. The pump set can have a first container configured to receiving breast milk; a second container configured to receive fortifier; tubing extending from the first container and from the second container; and a valve mechanism connected to the first and second containers by the tubing and configured to selectively pass liquid from the first container and the second container.

22 Claims, 6 Drawing Sheets

FEED-FORTIFY ENTERAL FEEDING AND RELATED METHODS THEREFOR

CROSS-REFERENCE TO RELATED APPLICATION

This application is a nonprovisional application of U.S. Serial No. 62/036,194, filed Aug. 12, 2014, the entire contents of which is incorporated herein by reference.

BACKGROUND

The present disclosure generally relates to an enteral feeding of breast milk and fortifier to an infant. Administering fluids containing medicine or nutrition to a patient is generally known in the art. Typically, fluid is delivered to the patient by a pump set received by a flow control apparatus, such as a pump, connected to a source of fluid which delivers fluid to a patient.

Currently, delivering breast milk and fortifier (e.g., formula) to an infant in a clinical setting requires a clinician to thaw a container of breast milk, measure a selected amount of fortifier based on a desired ratio to the amount of breast milk, then manually mix the breast milk and fortifier. This process can waste amounts of breast milk because the ratio of breast milk to fortifier desired may change before the mixture is used up. Because the breast milk is pre-mixed with the fortifier, the mixture may not be suitable for subsequent feedings. Further, the measurement process can be very time consuming. Additionally, this process can be messy since the mixture is prepared by hand, and the process also has the potential to transmit disease to the clinician since breast milk is known to carry blood borne pathogens.

SUMMARY

There is disclosed a method of delivering breast milk and fortifier to an infant using a pumping apparatus that acts on a pump set attached to the pumping apparatus to produce fluid flow through the pump set for delivery of the breast milk and fortifier to the infant. The method, in some cases, comprises receiving input into the pumping apparatus of a predetermined volume of breast milk to be delivered through the pump set to the infant; receiving input into the pumping apparatus of a predetermined volume of fortifier to be delivered through the pump set to the infant; operating the pumping apparatus according to the received input to deliver the predetermined volume of breast milk through the pump set at the selected breast milk flow rate; and operating the pumping apparatus according to the received input to deliver the predetermined volume of fortifier through the pump set at the selected fortifier flow rate.

There is also disclosed a pumping apparatus for use with a pump set to deliver breast milk and fortifier through the pump set to an infant. The pumping apparatus in some cases comprises a pumping device capable of acting on the pump set to produce a fluid flow within the pump set; and a controller in communication with the pumping device for controlling operation of the pumping device in a breast milk delivery configuration for producing a flow of breast milk in the pump set, and in a fortifier delivery configuration for producing a flow of fortifier in the pump set, the controller including a processor and a memory, the controller including a memory adapted to store a value representing amount of breast milk to be delivered through the pump set and a value representing an amount of fortifier to be delivered through pump set.

There is further disclosed a pump set for use with a pumping apparatus to deliver nutrition to an infant. The pump set can comprise a first container configured to receiving breast milk; a second container configured to receive fortifier; tubing extending from the first container and from the second container; and a valve mechanism connected to the first and second containers by the tubing and configured to selectively pass liquid from the first container and the second container. The first and second containers can be formed, in some cases, integrally with each other.

BRIEF DESCRIPTION OF THE DRAWINGS

Corresponding reference characters indicate corresponding parts throughout the drawings.

DETAILED DESCRIPTION

Figure 1:
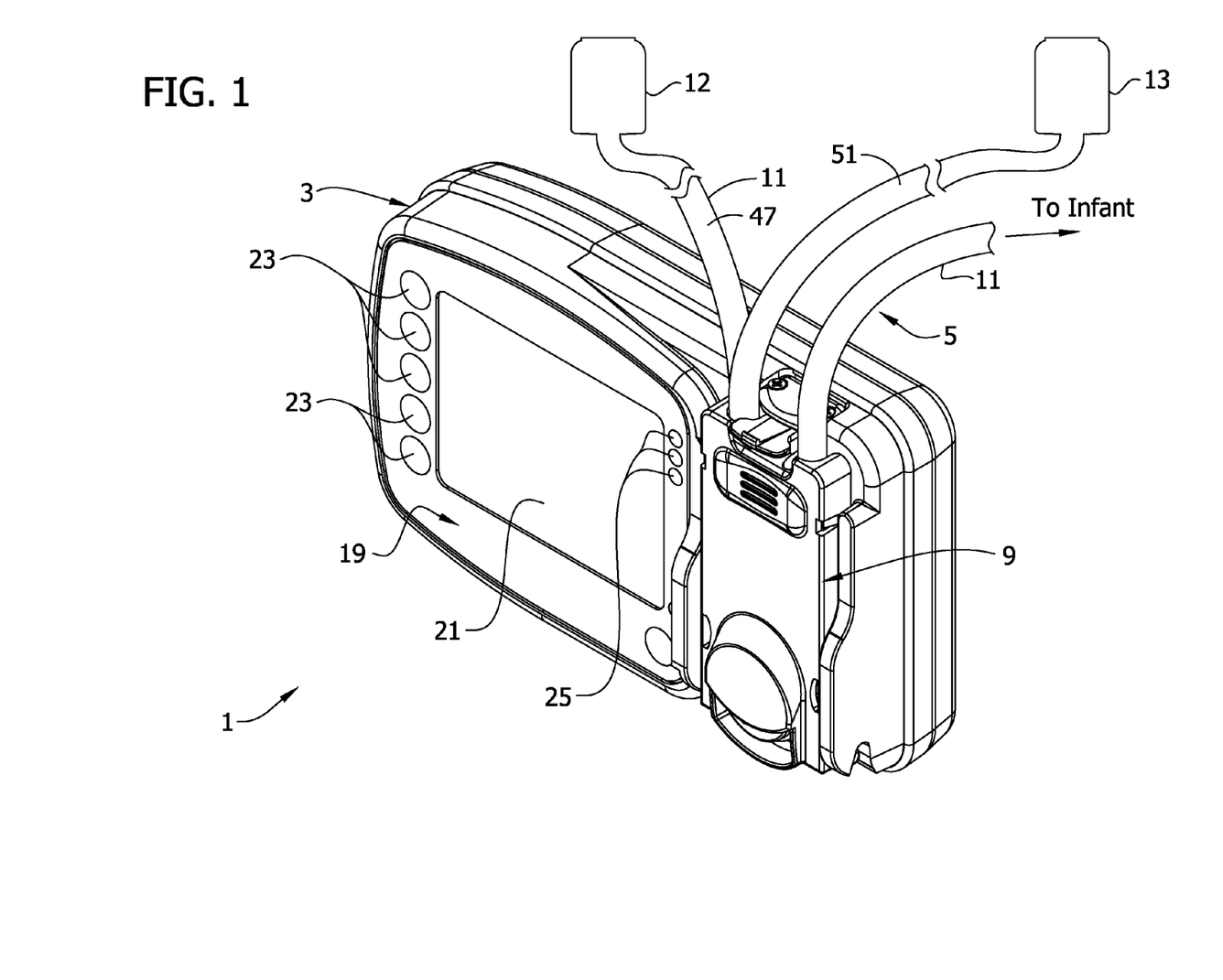
FIG. 1 is a schematic illustration showing a perspective view of an enteral feeding pump and a fragmentary portion of a feeding set (illustrated schematically) received on the pump.
Figure 2:
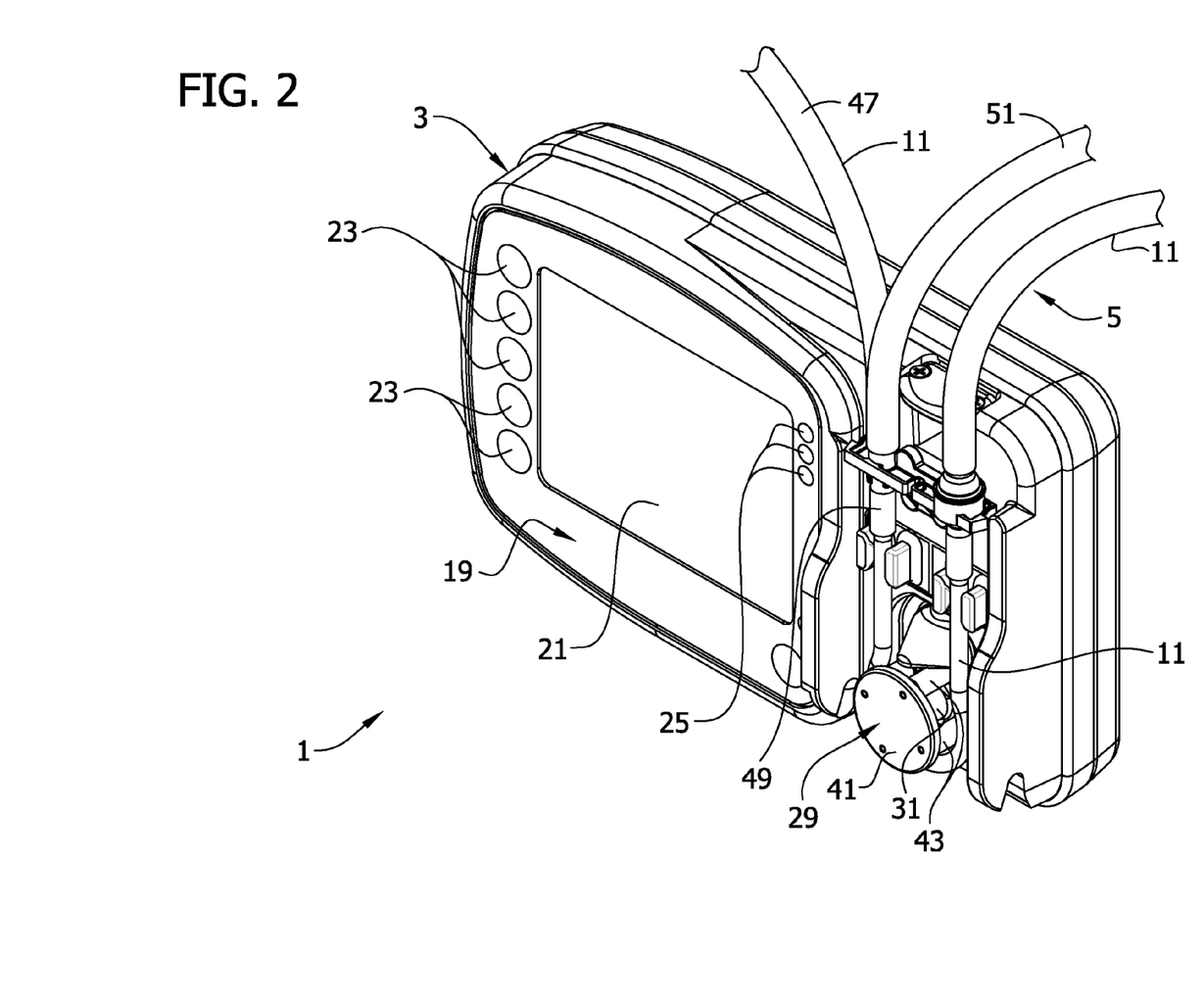
FIG. 2 is a schematic illustration showing a perspective view of the pump and set of FIG. 1 with a cassette housing of the feeding set removed.
Figure 3:
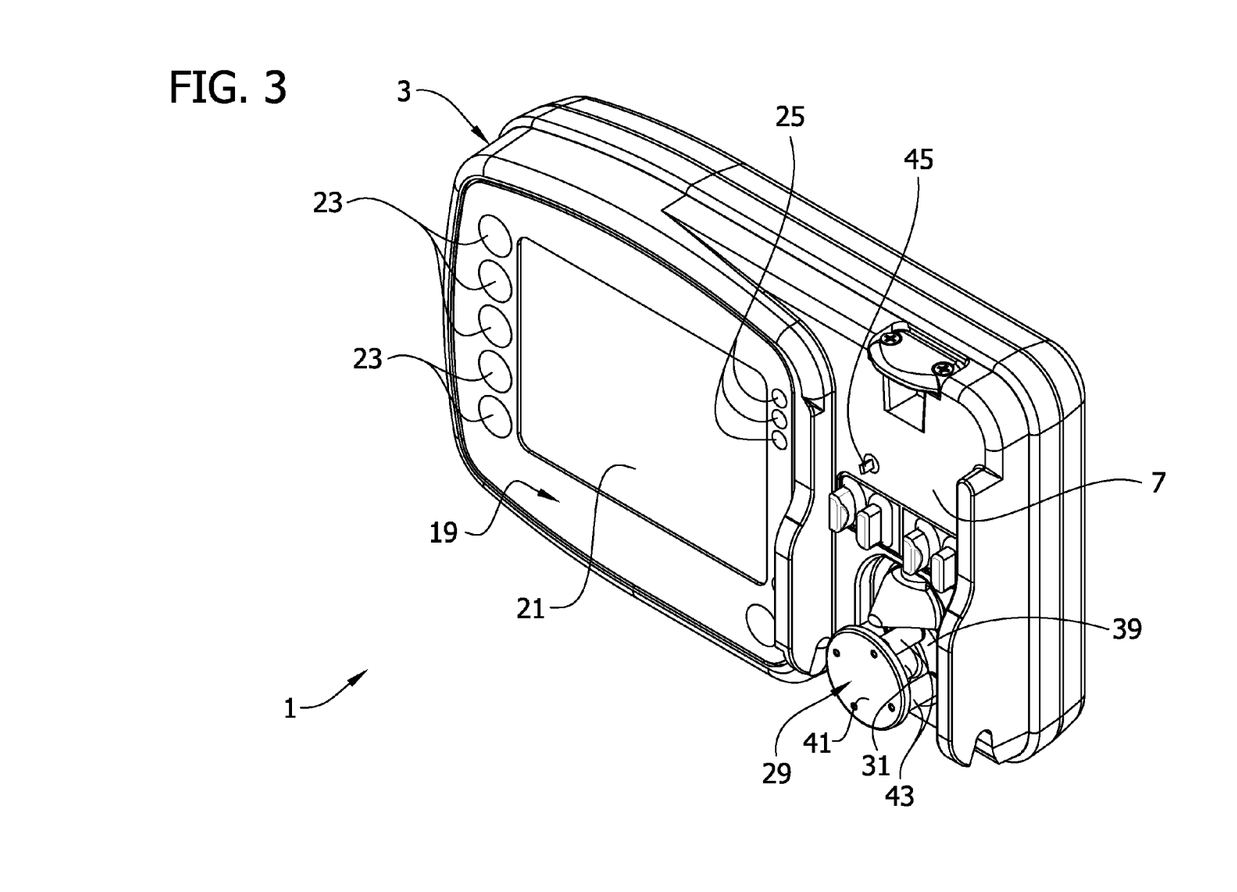
FIG. 3 is a schematic illustration showing a perspective view of the pump of FIG. 2 with the feeding set removed.

Referring now to the exemplary embodiment schematically illustrated in FIGS. 1, 2, and 3, an enteral feeding pump (broadly, "a flow control apparatus") is generally indicated at 1. The pump 1 may comprise a housing 3 that is constructed to allow an administration feeding set 5 (broadly, "a pump set") to be mounted to the housing. The housing 3 may comprise a recess 7 (FIG. 3) for receiving a cassette 9 of the feeding set 5 to load the feeding set on the pump. The feeding set 5 can comprise tubing indicated generally at 11 that provides a fluidic pathway between a first source of a first liquid such as a container or bag 12 of nutritional liquid (e.g., breast milk) and an infant (FIG. 1). The tubing 11 may also provide a fluidic pathway between a second source of a second liquid such as a container or bag 13 of fortifier (e.g., formula) and the infant. The fortifier can be a pre-mixed powdered formula mixed with water or a liquid fortifier. The cassette 9 may mount the tubing 11 for engaging the tubing with the pump 1 when the cassette is received in the recess 7. It will be understood that a pump set may have a construction other than shown herein without departing from the scope of the present disclosure. For example, a pump set (not shown) may not include a cassette 9 as illustrated herein.

Figure 1A:
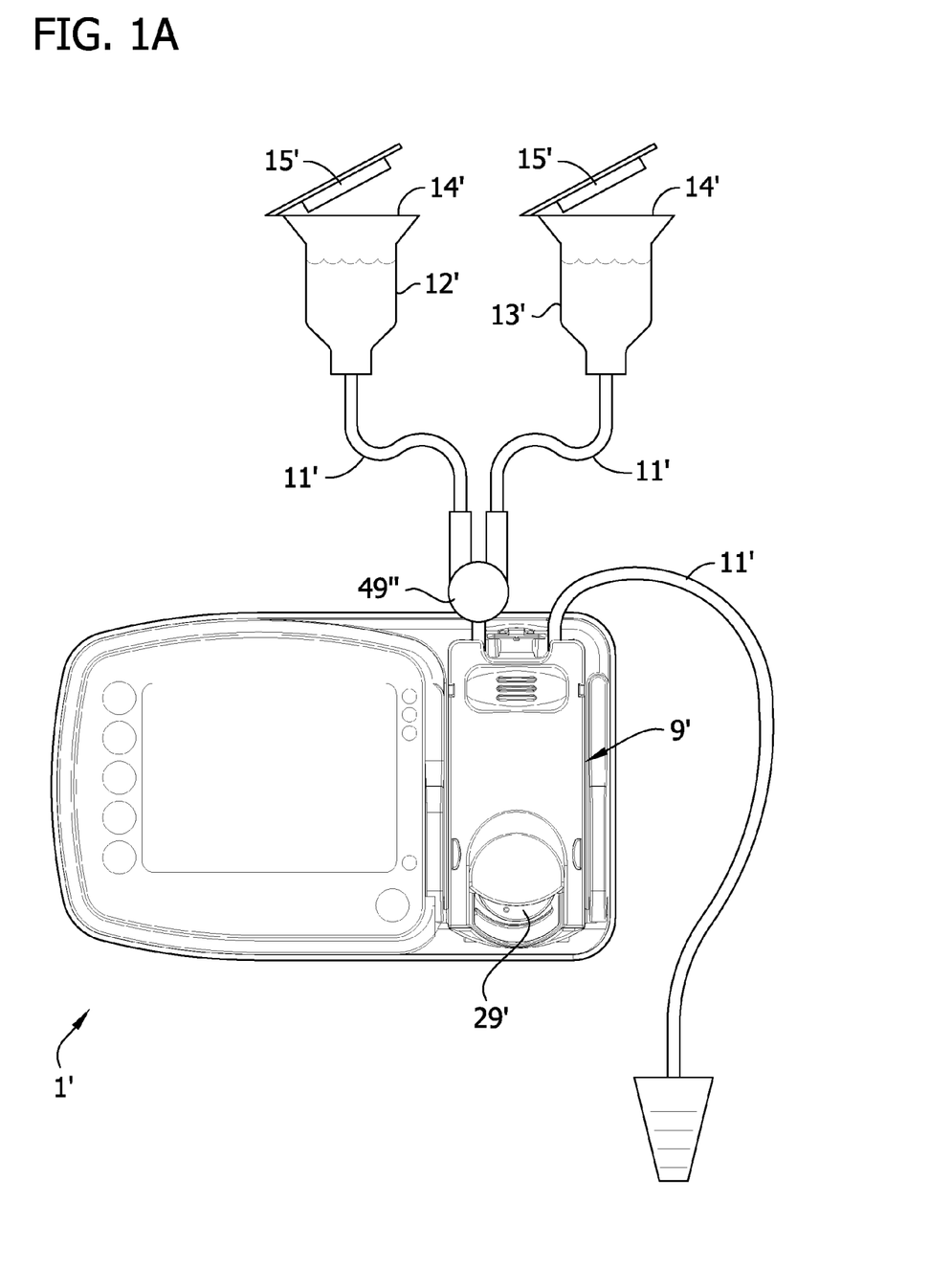
FIG. 1A is a schematic illustration of another enteral feeding pump and a feeding set loaded on the pump.
Figure 1B:
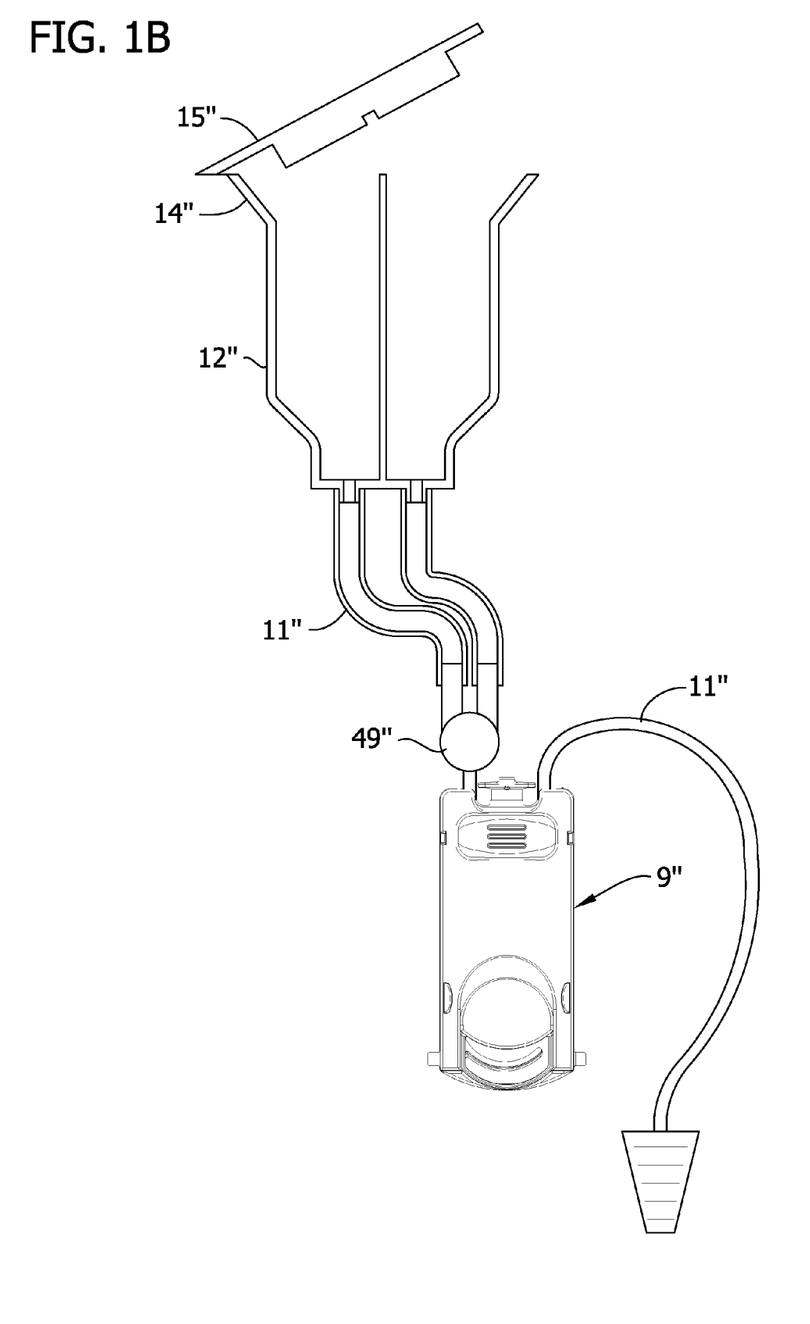
FIG. 1B is a schematic illustration of a feeding fluid container and tubing connected to a pumping device.

The bags 12, 13 are shown schematically in FIG. 1. In an embodiment, the bags 12, 13 may be rigid containers. For instance, FIG. 1A exemplarily shows a rigid container 12' including a flared top 14' and a lid 15' configured to snap on to the top of the container. The flared top 14' facilitates easy pouring of a liquid in the container 12' and the lid 15' seals the liquid in the container. The lid 15' may allow the container 12' and/or 13' to function as a storage container for the first and second liquids, such as breast milk and/or fortifier. One or both of the bags 12, 13 could be replaced with containers 12'. In FIG. 1A the bags 12, 13 are individually replaced with the rigid containers 12', 13'. In yet another embodiment, an integrated source of the first and second liquids can be utilized. Thus as illustrated, a bifurcated container 12" can be used to hold both the milk and fortifier (FIG. 1B). The bifurcated container 12" may also have a flared top 14" and snap on lid 15". Further, a dual lumen tubing 11" may connect outlets of the bifurcated container 12" to the pump 1.

The bag or container holding the breast milk may in one embodiment also be the same container used to collect the breast milk. This potentially eliminates s step involving a transfer of the breast milk between containers prior to delivery to the infant. As a result, the chance for contamination of the milk and/or exposure to the clinician of blood borne pathogens is reduced. This is extremely beneficial in neonatal intensive care units.

As used herein, the feeding set 5 being "received" by the pump 1 means that the tubing 11 is engaged with the pump 1 so that the feeding set is ready for operation with the pump to deliver liquid to a patient. The term "housing," as used herein, may include many forms of supporting structures including, without limitation, multi-part structures and structures that do not enclose or house the working components of the pump 1.

Referring back to FIGS. 1, 2, and 3, the pump 1 may include a user interface 19 with a display screen indicated at 21 on the front of the housing 3 that is capable of displaying information about the status and operation of the pump. The pump 1 can further comprise buttons 23 and light emitting diodes 25 on the housing 3 for use with the display screen 21 to facilitate exchanging information, such as providing and obtaining information, between the pump 1 and a user. Various user interfaces for displaying information to the user and receiving user input may be implemented. Any of the various configurations of the user interface can involve utilizing one or more graphical display subcomponents. As an example, the display screen 21 may be a graphical user interface having a touch screen by which the user can provide the input information. In other embodiments (not shown), the user interface can be a tethered component that can be used to provide input information, provide operating information pertaining to the flow control apparatus, or both.

Figure 4:
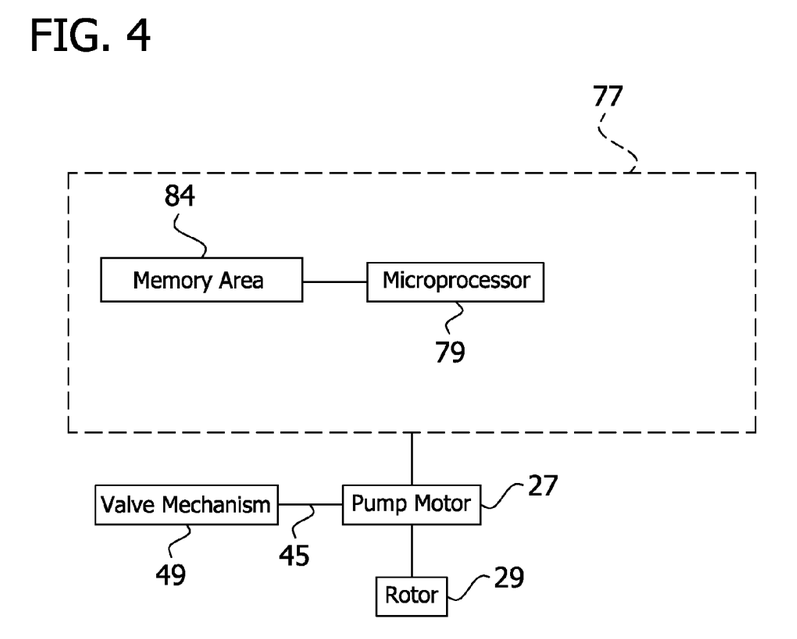
FIG. 4 is a block diagram showing components of the feeding pump that may be utilized to implement one or more aspects of the disclosure.

Referring to FIGS. 2-4, the pump 1 may include a pump motor 27 (FIG. 4) located in the housing 3. A pump rotor 29 may be mounted on a rotatable shaft 31 and rotated by the motor 27. In one embodiment, the pump rotor 29 includes an inner disk 39, an outer disk 41, and preferably a plurality of rollers 43 mounted between the inner and outer disks rotatable about their longitudinal axes relative to the disks. The motor 27 may also be connected to a valve shaft 45 (FIG. 3). It will be understood that the valve shaft 45 could be omitted, or a separate motor (not shown) could be provided to operate the valve shaft. The rollers 43 may engage the administration feeding set 5 for moving fluid, e.g., liquid, through the feeding set. In the illustrated embodiment, the pump motor 27, rotatable shaft 31, rotor 29, and valve shaft 45 may broadly be considered "a pumping device". It will be understood that peristaltic pumps that use mechanisms other than rollers may fall within the scope of the present disclosure. For example, a linear peristaltic pump could be used within the scope of the present disclosure. It is also envisioned that non-peristaltic pumps may be employed. Non-limiting examples of the cassette, apparatus, and controller therefor that may be utilized to implement one or more aspects disclosed herein include the systems and apparatus as disclosed in any of U.S. patent application Ser. No. 14/021,567, titled FEEDING SET WITH CASSETTE AND RELATED METHODS THEREFOR; U.S. patent application Ser. No. 14/472,521, based on U.S. patent application No. 61/871,944, titled FEEDING RATE COMPENSATED PUMP AND RELATED METHODS THEREFOR, and published as U.S. Patent Application Publication No. 2015/0065988 A1; U.S. patent application Ser. No. 14/807,495, based on U.S. patent application Ser. No. 62/028970, titled FLOW DETECTION SYSTEM FOR FLOW CONTROL APPARATUS, each of which is incorporated herein by reference for all purposes including, at least, utilizing for feeding, including operation and control, of the disclosed cassette, pump apparatus, and control system or controller.

Referring now to FIGS. 1, 2 and 4, the tubing 11 of the administration feeding set 5 provides a fluidic pathway for two liquid sources, bags 12 and 13, to communicate with an infant. A first inlet tube section 47 is connected at an inlet of the tubing 11 to bag 12 of breast milk and to valve mechanism 49 (FIG. 4). The valve mechanism may be a stopcock 49" (FIGS. 1A and 1B) or any other suitable mechanism for selectively switching between fluid sources. Operation of the valve mechanism 49 may be controlled by the pump device by way of connection of the valve mechanism 49 to the valve shaft 45.

A second inlet tube section 51 is connected at an inlet of the tubing 11 to bag 13 of fortifier and to the valve mechanism. The valve mechanism 49 is operable to selectively permit flow of breast milk from bag 12 or fortifier from bag 13, or prevent any fluid flow communication from the bags 12, 13 past the valve mechanism. Thus, the valve mechanism 49 can be turned to three positions. A first position closes off all liquid flow from the inlet tube sections 47, 51 past the valve mechanism 49. A second position allows breast milk to flow from bag 12 past the valve mechanism. A third position allows fortifier to flow from bag 13 past the valve mechanism. Alternatively, the pump 1 may simultaneously deliver a mixture of breast milk and fortifier from the bags 12, 13. In this embodiment, the valve mechanism 49, 49" could be configured to permit liquid flow from both bags 12, 13 at the same time. Moreover, a mixing device (not shown) could be incorporated into the feeding set to achieve mixing of the breast milk and fortifier. The mixing device can be a static mixer disposed at tubing 11 downstream from the pump, before introduction of the liquid to the infant. In use, the breast milk bag 12 and fortifier bag 13 can be suspended from a suitable support, such as an IV pole (not shown).

The pump 1 can be programmed or otherwise controlled for operation in a desired manner. For instance, the pump 1 can begin operation to provide breast milk from bag 12 to the infant or fortifier from bag 13 to the infant. The caregiver may select (for example) the amount of breast milk/fortifier to be delivered and the flow rate of the breast milk/fortifier. The pump 1 may have a controller 77 (FIG. 4) including a microprocessor 79 that allows it to accept programming and/or to include pre-programmed operational routines that can be initiated by the care giver. The controller 77 may also be connected to the pump motor 27 for controlling its operation to actuate the rotor 29 and to actuate the valve shaft 45 for actuating the valve mechanism 49. The pump motor 27 can operate the valve mechanism 49 and rotor 29 independently of each other.

If the pump 1 is to deliver breast milk from the bag 12 to the infant, the valve shaft 45 is rotated so that the valve mechanism 49 is moved to the second position in which fluid communication from the breast milk bag 12 past the valve mechanism is open and fluid communication from the fortifier bag 13 past the valve mechanism is closed. The pump 1 may be programmed or the care giver may select (for example) the amount of breast milk to be delivered to the infant and the flow rate at which the breast milk is to be delivered. The amount of breast milk that is delivered to the infant is controlled by the number of rotations of the rotor 29 (in a counterclockwise direction as viewed in FIG. 2).

In the illustrated embodiment, the rotor 29 may include the three rollers 43 so that each one-third of a rotation delivers one aliquot of liquid to the patient. As each roller 43 first engages the tubing 11, it pinches off the tubing thereby closing off an amount of liquid forward (i.e., toward the patient) from the liquid portion coming from the feeding fluid bag 12. The roller 43 continues to the right, pushing liquid forward of the roller toward the patient. Finally, the roller 43 releases engagement with the tubing 11 at about the same time the trailing roller engages the tubing for pinching it off for delivering the next aliquot of fluid. Thus, when the microprocessor 79 receives a command to deliver a selected fluid flow rate, it calculates the number of rotations within a given period of time that will deliver a number of aliquots producing the desired flow rate. It is to be understood that other ways of changing rotor operation could be used to maintain a constant flow rate. The selected flow rate may be a rate that is selected by the doctor, nurse or other care giver, or may be a default feeding rate pre-programmed into the pump 1.

If the pump 1 is to deliver fortifier from the bag 13 to the infant, the valve shaft 45 is rotated so that the valve mechanism 49 is moved to the third position in which fluid communication from the fortifier bag 13 past the valve mechanism is open and fluid communication from the breast milk bag 12 past the valve mechanism is closed. The amount of fortifier that is delivered through the tubing 11 is also controlled by the number of rotations of the rotor 29. The pump 1 may be programmed or the care giver may select (for example) the amount of fortifier to be delivered through the tubing and the rate at which the fortifier is to be delivered. A fortifier delivery cycle may operate at the programmed or selected interval after the breast milk delivery cycle is initiated/concluded. Additionally, a number of pre-set breast milk/fortifier ratios may be programmed into the microprocessor 79 to direct the amount breast milk and fortifier delivered to the infant.

As an example, if breast milk to fortifier ratio of 2:1 is selected, the pump will deliver a first volume of breast milk to the infant and a second volume of fortifier to the infant so that the overall delivery of nutritional liquid to the infant is in a 2:1 ratio. The microprocessor 79 may first instruct the valve shaft 45 to rotate the valve mechanism 49 to the second position to deliver breast milk from the breast milk bag 12. The pump 1 will deliver breast milk to the infant at the selected flow rate until the first volume of breast milk is delivered. The microprocessor 79 may then instruct the valve shaft 45 to rotate the valve mechanism 49 to the third position to deliver fortifier to the infant at the selected flow rate until the second volume of fortifier is delivered. At a ratio of 2:1, the pump 1 will deliver twice as much breast milk as fortifier to the infant. Other ratios are envisioned, including delivering only breast milk or only fortifier. Alternatively, the pump 1 may deliver the second volume of fortifier before the first volume of breast milk is delivered. The ratios may be based on a selected type and/or brand of fortifier.

It will also be understood that the pump 1 could be used as a feed/flush pump. In this configuration, bag 13 can be filled with water as the flushing liquid.

Accordingly, the controller 77 may comprise a memory area 84 for storing delivery ratios. The ratios may be pre-programmed into the pump memory area 84 or could be wirelessly or otherwise downloaded to the pump 1. The controller 77 may be programmed to deliver nutrition and different times in different ratios of breast milk to fortifier. Selection of the particular ratio of first liquid to second liquid may be based on several factors including but not limited to the hourly, daily, or weekly caloric requirements to be delivered to the patient, e.g., neonate, the fat requirements to be delivered, the time of delivery of the liquids, as well as requirements for specific nutritional components. For example, if a specified daily amount of calories may be set for a neonate to supplement the daily breast milk intake, then the ratio of the breast milk to the daily calorie target may be based on the amount of available breast milk relative to the caloric density of the supplemental second liquid, e.g., the fortifier.

Various aspects and embodiments disclosed herein may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Any of the various aspects may be implemented with any number and organization of such components or modules. For example, some disclosed aspects are not limited to the specific computer-executable instructions or the specific components or modules illustrated in the figures and described herein. Other embodiments and aspects may include different computer-executable instructions or components having more or less functionality than illustrated and described.

Further, the order of execution or performance of the operations exemplarily illustrated and described herein is not essential, unless otherwise specified. That is, the operations may be performed in any order, unless otherwise specified, and any of the disclosed embodiments may include additional or fewer operations than those disclosed herein. For example, it is contemplated that executing or performing a particular operation before, contemporaneously with, or after another operation is within the scope of aspects of the disclosure.

In operation, the microprocessor 79 executes computer-executable instructions to implement any of the various herein disclosed aspects. Any of the various aspects may also be practiced in distributed computing environments where tasks are performed by remote processing devices linked through a communications network. In a distributed computing environment, program modules may be located in both local and remote computer storage media including memory storage devices.

Having described the aspects and features in detail, it will be apparent that modifications and variations are possible without departing from the scope defined in the appended claims.

When introducing elements of the disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects are achieved and other advantageous results attained.

As various changes could be made in the above constructions and methods without departing from the scope, it is intended that all matter contained in the above description and shown in the accompanying drawings shall be interpreted as illustrative and not in a limiting sense.

What is claimed is:

1. A method of delivering breast milk and fortifier to an infant using a pumping apparatus that acts on a pump set attached to the pumping apparatus to produce fluid flow through the pump set for delivery of the breast milk and fortifier to the infant, the method comprising:
   receiving input into the pumping apparatus of a predetermined volume of breast milk to be delivered through the pump set to the infant;
   receiving input into the pumping apparatus of a predetermined volume of fortifier to be delivered through the pump set to the infant;
   executing instructions from a memory in the pumping apparatus to carry out a feeding in which breast milk and fortifier are fed by the pumping apparatus according to the input of the predetermined volume of breast milk and the input of the predetermined volume of fortifier; and during the feeding, pumping a volume of breast milk from a first nutritional liquid receptacle connected to the pumping apparatus and a volume of fortifier from a second nutritional liquid receptacle simultaneously connected to the pumping apparatus directly to the infant according to the received inputs at respective selected flow rates through the pump set attached to the pumping apparatus so that the volume of breast milk mixes with the volume of fortifier during the feeding.

2. A method as set forth in claim 1, wherein pumping the breast milk and fortifier to the infant comprises delivering the breast milk from a container used to collect the breast milk through the pumping apparatus to the infant.

3. A method as set forth in claim 1, wherein operating the pumping apparatus to deliver the predetermined volume of breast milk and fortifier comprises delivering the breast milk and fortifier at a pre-set breast milk to fortifier ratio programmed into a microprocessor of the pumping apparatus.

4. A method as set forth in claim 3, wherein the ratio of breast milk to fortifier is based on a caloric target for the infant.

5. A method as set forth in claim 3, wherein the ratio of breast milk to fortifier is based on a fat requirement for the infant.

6. A method as set forth in claim 3 wherein delivering the breast milk and fortifier at a pre-set breast milk fortifier ratio comprises turning with the pumping apparatus a valve mechanism to permit one of the breast milk and the fortifier to flow to the pumping apparatus for delivery to the infant at a rate and over a period of time corresponding to a selected ratio of breast milk and fortifier, and then turning with the pumping apparatus the valve mechanism to permit the other of the breast milk and fortifier to flow to the pumping apparatus for delivery to the infant at a rate and over a period of time corresponding to the selected ratio of breast milk and fortifier.

7. A method as set forth in claim 3 wherein delivering the breast milk and fortifier at a pre-set breast milk fortifier ratio comprises turning with the pumping apparatus a valve mechanism to permit the breast milk and fortifier to flow at the same time through a valve mechanism in a selected ratio of breast milk and fortifier.

8. A method as set forth in claim 1 wherein operating the pumping apparatus to deliver the predetermined volume of breast milk and fortifier comprises operating the pumping apparatus at different times to deliver breast milk and fortifier in different ratios.

9. A pumping apparatus for use with a pump set to deliver breast milk and fortifier through the pump set to an infant, the pumping apparatus comprising:
   a housing;
   a pumping device mounted on the housing and capable of acting on the pump set to produce a fluid flow within the pump set;
   a controller in communication with the pumping device for controlling operation of the pumping device in a breast milk delivery configuration for producing a flow of breast milk in the pump set, and in a fortifier delivery configuration for producing a flow of fortifier in the pump set, the controller including a processor and a memory, the memory storing a value representing amount of breast milk to be delivered through the pump set and a value representing an amount of fortifier to be delivered through the pump set; and
   a valve shaft extending from the housing and configured to engage a valve mechanism of the pump set to move the valve mechanism between multiple positions, at least one of the multiple positions permitting only breast milk to flow to the infant and at least another of the multiple positions permitting only fortifier to flow to the infant, the controller being configured to control operation of the valve shaft to control the flow of breast milk and fortifier to the pumping apparatus to achieve the value representing the amount of breast milk and the value representing the amount of fortifier to be delivered through the pump set to the infant.

10. A pumping apparatus as set forth in claim 9, wherein the value representing amount of breast milk to be delivered through the pump set and the value representing an amount of fortifier to be delivered through pump set is based on a pre-set breast milk to fortifier ratio programmed into the processor and stored in the memory.

11. A pumping apparatus as set forth in claim 10, wherein the ratio of breast milk to fortifier is based on a caloric target for the infant.

12. A pumping apparatus as set forth in claim 10, wherein the ratio of breast milk to fortifier is based on a fat requirement for the infant.

13. A pumping apparatus as set forth in claim 9 wherein the controller is configured to deliver the breast milk and the fortifier at a pre-set breast milk fortifier ratio by turning the valve mechanism with the valve shaft to permit one of the breast milk and the fortifier to flow to the pumping apparatus for delivery to the infant at a rate and over a period of time corresponding to a selected ratio of breast milk and fortifier, and then turning the valve mechanism with the pumping apparatus to permit the other of the breast milk and the fortifier to flow to the pumping apparatus for delivery to the infant at a rate and over a period of time corresponding to the selected ratio of breast milk and fortifier.

14. A pumping apparatus as set forth in claim 9 wherein the controller is configured to deliver the breast milk and fortifier at a pre-set breast milk fortifier ratio by turning with the pumping apparatus a valve mechanism to permit the breast milk and fortifier to flow at the same time through the valve mechanism in a selected ratio of breast milk and fortifier.

15. A pumping apparatus as set forth in claim 9 wherein the controller is configured to operate the pumping apparatus to deliver the predetermined volume of breast milk and fortifier by operating the pumping apparatus at different times to deliver breast milk and fortifier in different ratios.

16. The pumping apparatus as set forth in claim 9, wherein the controller includes instructions stored in the memory to carry out a feeding to deliver a volume of breast milk from a first nutritional liquid receptacle connected to the pumping device and a volume of fortifier from a second nutritional liquid receptacle simultaneously connected to the pumping device directly to the infant according to received inputs at respective selected flow rates through the pump set attached to the pumping device so that the volume of breast milk mixes with the volume of fortifier during the feeding.

17. A pump set for use with a pumping apparatus to deliver nutrition to an infant, the pump set comprising:
- a first container having a removable lid and being configured to receiving breast milk;
- a second container having a removable lid and being configured to receive fortifier;
- tubing extending from the first container and from the second container; and
- a valve mechanism connected to the first and second containers by the tubing and configured to selectively pass liquid from the first container and the second container by allowing liquid to pass from the first container while blocking liquid from passing from the second container, and allowing liquid to pass from the second container while blocking liquid from passing from the first container, wherein the valve mechanism is constructed to allow fluid to pass from both the first and the second container simultaneously.

18. A pump set as set forth in claim 17, wherein the first and second containers are formed integrally with each other.

19. A method as set forth in claim 1, wherein pumping breast milk and fortifier directly to the infant comprises simultaneously pumping breast milk and fortifier directly to the infant.

20. A pump set as set forth in claim 17, wherein at least one of the first and second containers includes a flared top and wherein the lid is configured to snap on to the top of said container.

21. A pump set as set forth in claim 17, wherein the tubing comprises a dual lumen tubing.

22. A pump set as set forth in claim 17, wherein the first container is configured for use in collection of the breast milk such that there is no transfer of breast milk between multiple containers prior to delivery to the infant.

* * * * *